US009474636B2

(12) United States Patent
Sandahl et al.

(10) Patent No.: US 9,474,636 B2
(45) Date of Patent: Oct. 25, 2016

(54) VALVE FOR PROSTHETIC DEVICE

(71) Applicant: OSSUR HF, Reykjavik (IS)

(72) Inventors: David Sandahl, Reykjavik (IS);
Hafsteinn Jonasson, Mosfellsbær (IS)

(73) Assignee: OSSUR HF, Reykjavik (IS)

( * ) Notice: Subject to any disclaimer, the term of this patent is extended or adjusted under 35 U.S.C. 154(b) by 0 days.

(21) Appl. No.: 14/658,338

(22) Filed: Mar. 16, 2015

(65) Prior Publication Data

US 2015/0265433 A1    Sep. 24, 2015

Related U.S. Application Data

(60) Provisional application No. 61/955,880, filed on Mar. 20, 2014.

(51) Int. Cl.
*A61F 2/80*    (2006.01)
*F16K 7/06*    (2006.01)
*A61F 2/60*    (2006.01)

(52) U.S. Cl.
CPC . *A61F 2/80* (2013.01); *A61F 2/60* (2013.01); *A61F 2002/805* (2013.01)

(58) Field of Classification Search
CPC .............. A61F 2/80; A61F 2002/802; A61F 2002/805; A61F 2002/807; B65D 90/34; A61M 16/208; A61M 16/108; F16K 7/06
USPC .......................... 623/34; 137/855, 856, 527.6
See application file for complete search history.

(56) References Cited

U.S. PATENT DOCUMENTS

| 2,530,285 | A | 11/1950 | Catranis |
| 2,569,790 | A * | 10/1951 | White ........................ A61F 2/80 |
| | | | 137/533.27 |
| 4,595,172 | A | 6/1986 | Henderson |
| 4,655,779 | A | 4/1987 | Janowiak |
| 5,885,509 | A | 3/1999 | Kristinsson |
| 6,136,039 | A | 10/2000 | Kristinsson et al. |
| 6,358,222 | B1 | 3/2002 | Grundei |
| 6,485,776 | B2 | 11/2002 | Janusson et al. |
| 6,613,096 | B1 | 9/2003 | Shirvis |

(Continued)

FOREIGN PATENT DOCUMENTS

AT    164884 B    12/1949
EP    1 875 881 A1    1/2008

OTHER PUBLICATIONS

International Search Report from Corresponding International PCT Application No. PCT/US2015/020657, Jun. 2, 2015.

*Primary Examiner* — Bruce E Snow
(74) *Attorney, Agent, or Firm* — Workman Nydegger

(57) ABSTRACT

A valve for use with a prosthetic socket includes a body defining an upper opening, a lower opening adapted to be in fluid communication with the socket cavity, and a passageway formed between the openings. A membrane is flexibly seated on the body over the upper opening. The membrane is moveable between a closed position in which the upper opening is sealed such that fluid communication between the upper opening and the lower opening is inhibited, and an open position in which the upper opening is unsealed such that fluid can flow through the passageway. The membrane includes a first part connected to a release element that is operable to move the membrane between the open and closed positions, and a free part operable independent of the first part to move the membrane between the open and closed positions.

19 Claims, 4 Drawing Sheets

(56) References Cited

U.S. PATENT DOCUMENTS

| | | |
|---|---|---|
| 6,626,952 B2 | 9/2003 | Janusson et al. |
| 6,706,364 B2 | 3/2004 | Janusson et al. |
| 7,001,563 B2 | 2/2006 | Janusson et al. |
| 7,105,122 B2 | 9/2006 | Karason |
| 7,118,602 B2 | 10/2006 | Bjarnason |
| 7,993,413 B2 | 8/2011 | Perkins et al. |
| 8,382,852 B2 | 2/2013 | Laghi |
| 9,086,162 B2 * | 7/2015 | Chaffee ............... A47C 27/081 |
| 2010/0087931 A1 | 4/2010 | Bogue |
| 2013/0282142 A1 | 10/2013 | Perkins et al. |

* cited by examiner

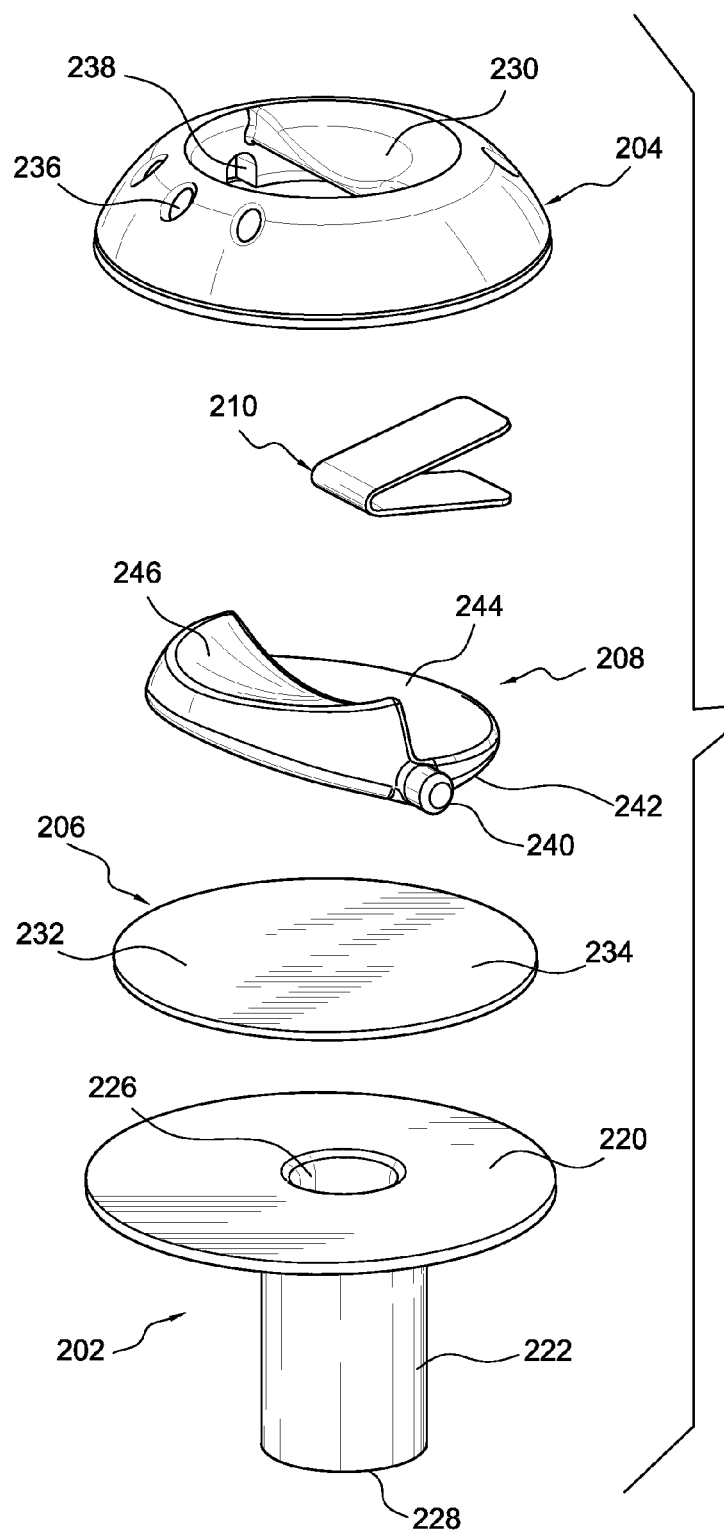

VALVE FOR PROSTHETIC DEVICE

TECHNICAL FIELD

The disclosure relates to a valve for a prosthetic device.

BACKGROUND

Amputees can secure prosthetic devices on their residual limbs by using various vacuum or suction arrangements, whereby the maximum strength of the force holding the prosthesis to the residual limb is a function of the atmospheric pressure. The differential air pressure is routinely referred to as suction or vacuum by those having skill in the art. To maintain the sub-atmospheric pressure created within the distal end of the socket, sealing sleeves or liners have been provided to prevent an influx of air around the distal end of the residual limb. Such liners are provided between the residual limb and the socket to provide for slight compression, and a gripping connection is provided to assist with the suction suspension.

The liner can be rolled onto the residual limb so the liner-covered limb can then be inserted into the prosthetic socket. Using conventional liners alone only provides a partial suction fit since they form no true air-tight seal with the socket. Some air will slowly enter the socket, especially during the swing phase of the patient's gait and during periods of inactivity.

Using a valve should allow air to be expelled from the socket in order to maintain at least a slight negative pressure for creating the suction against the residual limb. Although the swing phase of the gait cycle will pull the socket off the limb, walking and other weight-bearing activities may push the limb further into the socket. Pushing the limb further into the socket causes the valve to expel air. Conversely, directly pulling the limb out of the socket is prohibited due to the effect of suction. Using a valve is also helpful in preventing a positive pressure within the socket interior relative to the ambient air outside the socket to allow donning the prosthesis on a limb. Common valve systems used with sockets have included a valve member mounted in a cavity that moves between a sealed position and a vented position and a biasing member biasing the valve member to its seated position.

Unfortunately, conventional valve systems such as these suffer from several drawbacks. For instance, such systems often delay a tight and secure fit as a prosthetic user dons the socket because of poor air flow and air resistance. The poor air flow and air resistance of such valve systems also can decrease the suction applied to the residual limb, which may cause it to become disengaged during use. Many existing valve systems include components protruding from the socket, making it cumbersome and uncomfortable to wear, while also increasing the chance it may snag onto foreign objects. By not keeping a low profile, there is also a greater likelihood of the valve system being damaged. The sealing strength of such valve systems can also be insufficient or limited. Damaging the valve or compromising the seal strength would cause the air pressure within the socket to no longer be properly maintained, and the suspension it provides to the residual limb would ultimately fail.

In view of the shortcomings of conventional valve systems, there exists a substantial need for a valve that improves suspension and makes it easier to don and doff a socket.

SUMMARY

Embodiments of the valve for a prosthetic device provide the capacity to expel and/or introduce air into a socket with little air resistance and good air flow. By improving air flow and reducing air resistance, the embodiments improve suspension and avoid the risk of undesirable pressure differentials that can adversely affect donning and doffing.

It is a goal of the present disclosure to offer a fast and efficient way to regulate the level of extraneous air within a socket. By providing a valve with a membrane having different portions that operate efficiently and independently and in response to different triggers, a user can adjust the desired level of air within a socket on the fly during use or when initially donning the prosthesis. It should be appreciated the valve of various embodiments can utilize a single membrane and a low-profile housing. This allows the valve to keep a low profile so a user does not have to worry about constantly bumping or snagging the valve on foreign objects.

It is another goal of the present disclosure to offer a fast and efficient way to expel air from interior of a socket. The valve of various embodiments offers a practical solution for a patient who would otherwise need to adjust their limb in the socket and apply weight repeatedly in order to evacuate the socket. By reducing air resistance and improving air flow through the valve as in the embodiments, air can be more quickly expelled from a socket and the number of steps required for a tight fit while donning the socket are substantially reduced.

In an embodiment, a valve for use with a prosthetic socket includes a body defining a upper opening, a lower opening adapted to be in fluid communication with the socket cavity, and a passageway formed between the openings. A membrane can be flexibly seated on the body over the upper opening. The membrane can be moveable between a closed position which the upper opening is sealed such that fluid communication between the upper opening and the lower opening is inhibited, and an open position in which the upper opening is unsealed such that air can flow through the passageway. The membrane may include a first part connected to a release element that is operable to move the membrane between the open and closed positions and a free part that is operable independent of the first part to move the membrane between the open and closed positions. The first part can move the membrane to the open position in response to movement of the release element and the free part can move the membrane to the open position in response to buildup of pressure inside of the rigid socket.

Additional features and advantages of embodiments of the present disclosure will be set forth in the description that follows, and in part will be obvious from the description, or may be learned by the practice of such exemplary embodiments. These and other features will become more fully apparent from the following description and appended claims, or may be learned by the practice of such exemplary embodiments as set forth.

BRIEF DESCRIPTION OF THE DRAWINGS

These and other features, aspects, and advantages of the present disclosure will become better understood regarding the following description, appended claims, and accompanying drawings.

FIG. 4 is an exploded view of the valve in FIG. 2 according to an embodiment.

DETAILED DESCRIPTION

Figure 1:
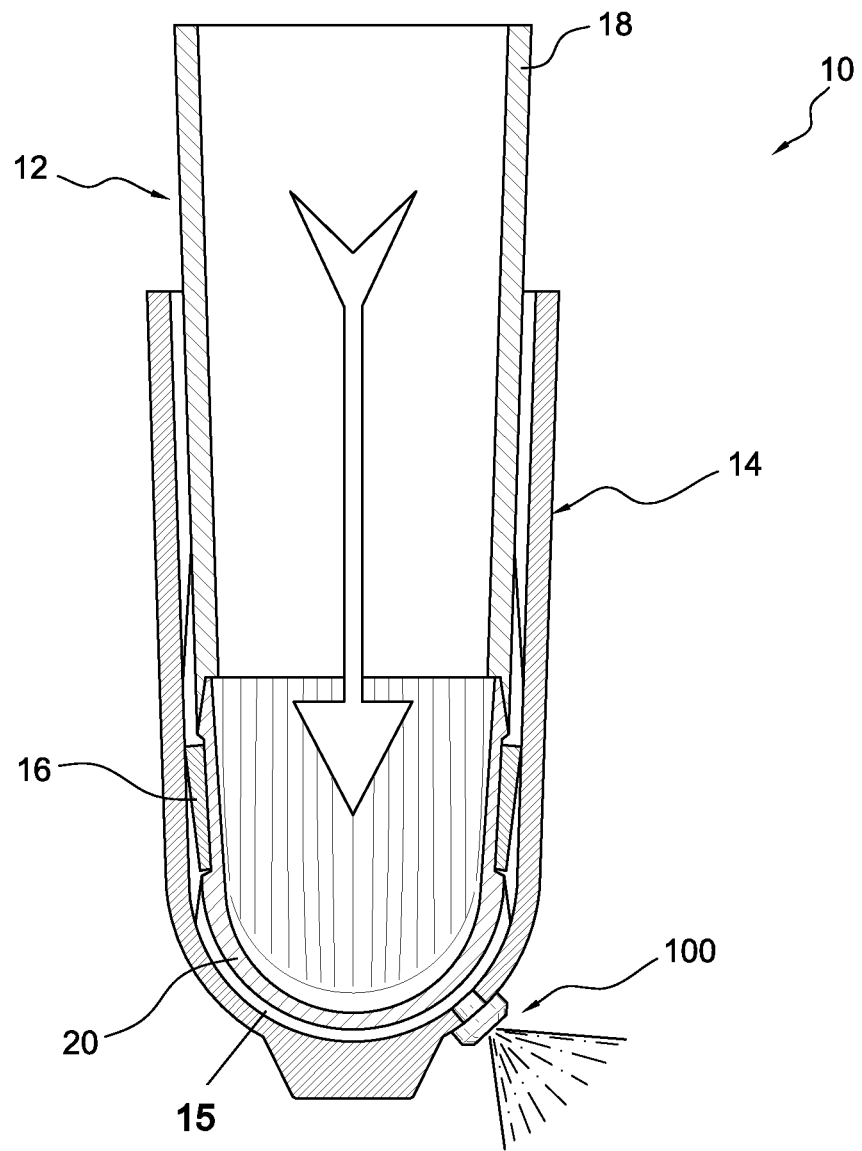
FIG. 1 is a schematic view of a prosthetic socket system according to an embodiment.

A better understanding of different embodiments of the disclosure may be had from the following description read with the accompanying drawings in which like reference characters refer to like elements.

While the disclosure is susceptible to various modifications and alternative constructions, certain illustrative embodiments are in the drawings and are described below. It should be understood, however, there is no intention to limit the disclosure to the embodiments disclosed, but on the contrary, the intention covers all modifications, alternative constructions, combinations, and equivalents falling within the spirit and scope of the disclosure.

It will be understood that unless a term is defined in this patent to possess a described meaning, there is no intent to limit the meaning of such term, either expressly or indirectly, beyond its plain or ordinary meaning.

The valve system described is configured for use with a prosthetic socket, such as lower leg prosthesis. It should be remembered, however, that the same concepts and methods described may be similarly used for other prosthetic devices and are not limited solely to the anatomical locations discussed.

The terms "proximal" and "distal" generally refer to areas on the prosthetic socket that correspond to a location relative to where a residual limb can be inserted. For instance, the proximal end of the socket is its open end where a residual limb is first inserted into. The distal end of the socket is opposite the proximal end and includes at least part of a cavity of the socket arranged to receive a residual limb.

Any element in a claim that does not explicitly state "means for" performing a specified function, or "step for" performing a function is not to be interpreted as a "means" or "step" clause as specified in 35 U.S.C. §112, paragraph 6.

As shown in FIG. 1, embodiments of the valve can be employed with a prosthetic socket system 10. The prosthetic socket system 10 can include an elastomer liner sleeve 12, a prosthetic socket 14, and a valve 100. The elastomer liner sleeve 12 can extend between a proximal end 18 and a distal end 20. The liner sleeve 12 is typically donned on a residual limb and the limb and sleeve 12 are then inserted into a socket cavity 15 defined by the prosthetic socket 14. The socket 14 is typically rigid or hard to carry loads transferred from a prosthetic device attached to the socket 14 to the residual limb and vice-versa.

The softer elastomer of the liner sleeve 12 adheres to the skin of the residual limb frictionally to secure the limb within the sleeve 12. The liner sleeve 12 remains within the rigid socket 14 after it has been fully inserted into the distal end area of the rigid socket 14 by isolating the interior of the rigid socket 14 from atmosphere. Pulling forces applied to the liner sleeve 12 will cause a suction being created between the distal end of the liner sleeve 12 and the interior of the socket 14 at the distal end area. Besides assisting with suction inside the socket 14 so the residual limb does not fall out, the liner sleeve 12 may also provide cushioning to the limb. Using the liner sleeve 12 to provide a tight fit for the residual limb within the socket 14 also helps to prevent air from entering the socket interior from outside of the socket 14.

An example of a socket and method for making the same are found in U.S. Pat. No. 5,885,509, granted Mar. 23, 1999, and U.S. Pat. No. 7,105,122, granted Sep. 12, 2006, both incorporated by reference. An exemplary liner sleeve for combination with the socket is found in U.S. Pat. No. 6,136,039, granted Oct. 24, 2000, U.S. Pat. No. 6,626,952, granted Sep. 30, 2003, U.S. Pat. No. 6,485,776, granted Nov. 26, 2002, U.S. Pat. No. 6,706,364, granted Mar. 16, 2004, U.S. Pat. No. 7,001,563, granted Feb. 21, 2006, and U.S. Pat. No. 7,118,602, granted Oct. 10, 2006, each of which are incorporated by reference in their entirety.

If the liner sleeve 12 provides no true air-tight seal with the socket 14, some air will slowly enter the socket interior during use. The presence of additional air within the socket 14 would disrupt the pressure differential between the inside of the socket 14 and the surrounding ambient air outside the socket 14 decreasing the suction and potentially causing the limb to become disengaged from the socket.

To further enhance isolation of the distal end area of the inside of the socket 14 from atmosphere, a seal element 16 may be between the liner sleeve 12 and the inner surface of the socket 14. The sealing element 16 is configured to provide an increased sealing force between the liner sleeve 12 and the socket 14 when the liner sleeve 12 is moved in a direction tending to withdraw it from the socket 14. When the distal end of the liner sleeve 12 is fully inserted into the socket 14, the sealing element 16 further isolates the inside of the socket 14 from ambient air outside the socket 14 until communication is provided between the inside of the socket distal end and atmosphere. If desired, a hypobaric pressure could be created between the distal end area of the liner sleeve 12 and the distal end of the socket 14 by attaching a pump or other device that enables evacuation of atmosphere between the sealing element 16 and the distal end of the socket 14.

The socket 14 can define an aperture extending between the interior and the exterior of the socket 14. A valve 100 can be provided at the aperture to control fluid flow between the interior and the exterior of the socket 14. The valve 100 is shown within the wall of the socket 14 near the distal end area of the socket 14, but may also be near other areas on the socket 14 as desired if the valve 100 remains in fluid communication with an interior portion of the socket 14 where the prosthetic user's residual limb resides.

The valve 100 can include a membrane having a flexible configuration that controls flow through the valve 100. The membrane can have different portions that operate independently and in response to different triggers or events to more efficiently and effectively control the level of extraneous air within the socket 14. The membrane can include a first or an attached part attached to a release element and a free part not attached to the release element. The attached part can be controlled and operated to introduce fluid or air and/or relieve pressure inside of the socket 14 and the free part can be independently and automatically relieve a buildup of pressure inside of the socket 14.

To prevent air flow through the valve 100, the free part and the attached part can be both in a closed position. To allow air flow through the valve 100, one or both of the attached part and the free part can be actuated or in an open position. The free part of the membrane is configured such that it is actuated by positive pressure inside of the socket 14. The attached part is configured such that it actuated by movement of the release element. When the free part is actuated, the attached part is not actuated, and vice versa. This advantageously provides enhanced control of air flow through the valve 100.

It will be appreciated that the free part is not under the influence of an opposing biasing force or member, as in the prior art. This advantageously helps to reduce air resistance over the valve 100. This also helps to improve air flow through the valve 100. Easy donning can be accomplished since air may be automatically and efficiently expelled as the residual limb is inserted into the socket. This is because the volume of the residual limb displaces the volume of air inside the socket 14, forcing the free part of the membrane to actuate and forcing the remaining air out through the valve 100. Any fluid or air expelled through the valve 100 cannot re-enter the socket 14 through the same channel, unless the attached part of the membrane is independently actuated by a user. The improved air flow and reduced air resistance also permits faster donning while still providing a snug fit for the residual limb. This also allows the socket 14 to be donned in one motion or a few steps rather than having to repeatedly apply weight to evacuate the socket 14, as in the prior art.

The membrane is arranged such that positive pressure inside the socket 14 helps unseal the free part to expel air from the socket 14 and negative pressure inside the socket 14 helps seal the free part and the attached part to preserve the suspension fit of the residual limb within the socket 14. The membrane is also configured such that the membrane forms a flow path that generally directs air traveling through the valve 100 toward exit apertures, improving air flow and reducing air resistance.

Figure 2:
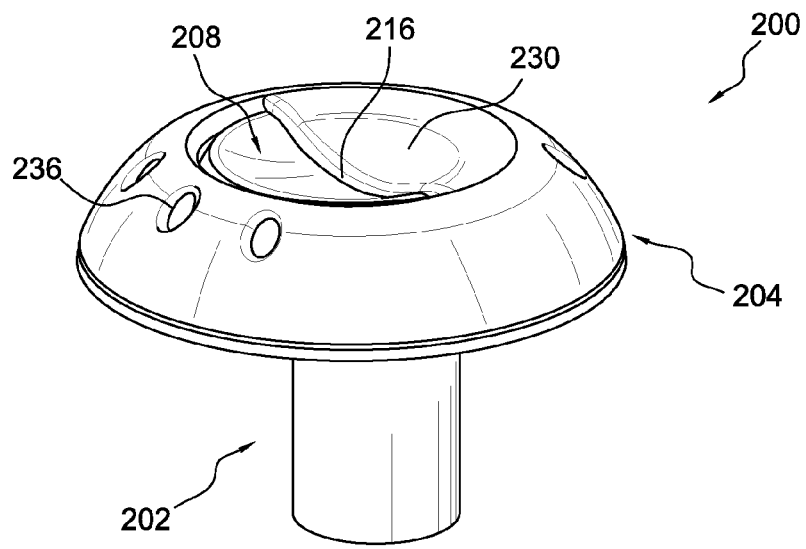
FIG. 2 is an isometric view of a valve according to an embodiment.

FIGS. 2-4 illustrate an embodiment of a valve 200. The valve 200 can include a body 202, a housing 204, a membrane 206 having a flexible configuration, a release element 208, and a resilient member 210. As seen in FIG. 2, the housing 204 may have a low-profile dome-like shape and may be attached on the body 202. Since the housing 204 has a low profile, there is less chance of the valve 200 getting knocked off a socket or damaged because of bumping into foreign objects. Because of the dome-like shape, there is also less chance of the valve 200 snagging on foreign objects. The housing 204 can form an interference fit, a friction fit, and/or any other suitable attachment with the body 202.

An interior surface 212 of the housing 204 can define an interior cavity 214 (shown in FIG. 3A) over the body 202. The membrane 206, release element 208, and the resilient member 210 can be inserted in the interior cavity 214. A housing opening 216 (shown in FIG. 2) can extend between an exterior surface 218 of the housing 204 to the interior surface 212 of the housing 204. The housing opening 216 can provide access to the release element 208. The exterior surface 218 of the housing 204 can include an ergonomic, concave recess 230. The housing opening 216 can be positioned in the concave recess 230. This can help protect the release element 208 from being caught or inadvertently bumped. This can also allow the release element 208 to be comfortably pressed and released. It will be appreciated that while the housing 204 is described having a dome-like shape, an opening, and concave recess, embodiments of the housing can have any suitable shape, size, and/or feature.

Referring now to FIGS. 3-4, the body 202 can include a base 220 and a shaft 222 connected to the base 220. The shaft 222 can extend generally traverse to the base 220. The shaft 222 can be adapted to mount the valve 200 onto a socket. The shaft 222 can be adapted to extend into an aperture formed through the wall of a socket for fluid communication with the interior of the socket. Alternatively, the shaft 222 can be adapted to mount the valve 200 to a fitting and/or tube used for coupling the valve 200 to the socket. It will be appreciated that the shaft 222 can have any shape and/or size suitable for mounting the valve 200.

The body 202 can define a passageway 224 extending between an upper opening 226 formed in the upper surface of the base 220 and a lower opening 228 formed in the free end of the shaft 222. The passageway 224 can have a circular cross-section, an elliptical cross-section, a hexagonal cross-section, or any other suitable cross-section shape. The passageway 224 can have a constant diameter or a varying diameter.

Flow through the passageway 224 is controlled by the membrane 206 inserted in the interior cavity 214 of the housing 204. The membrane 206 can be a flexible disc member seated on the base 220 over the upper opening 226. The membrane 206 may comprise an elastomeric material, a synthetic rubber, a fluoropolymer elastomer, and other sealing element materials and/or configurations may be employed.

The membrane 206 can have different portions that operate independently and in response to different triggers or events to more effectively and efficiently control the level of extraneous air within a socket. The membrane 206 can include an attached part 234 attached to the release element 208 and a free part 232 not attached to the release element 208. The attached part 234 of the membrane 206 can be manually controlled and operated to allow air flow through the passageway 224. The free part 232 of the membrane 206 can independently and automatically to allow air flow out of the valve 200 through the passageway 224 in response to an increase or buildup of pressure inside of the socket. This advantageously allows the valve 200 to more efficiently and effectively control the level of air within a socket in a wider variety of situations.

The membrane 206 can move between a closed position (seen in FIG. 3A), wherein the upper opening 226 is sealed and air flow through the passageway 224 is inhibited, and an open position, wherein the upper opening 226 is unsealed such that air can flow through the passageway 224. The open position can include a first open position (seen in FIG. 3B), wherein the upper opening 226 is unsealed by the free part 232 of the membrane 206 such that air can flow through the passageway 224; and a second open position (seen in FIG. 3C), wherein the upper opening 226 is unsealed by the attached part 234 of the membrane 206 such that air can flow through the passageway 224.

Figure 3A:
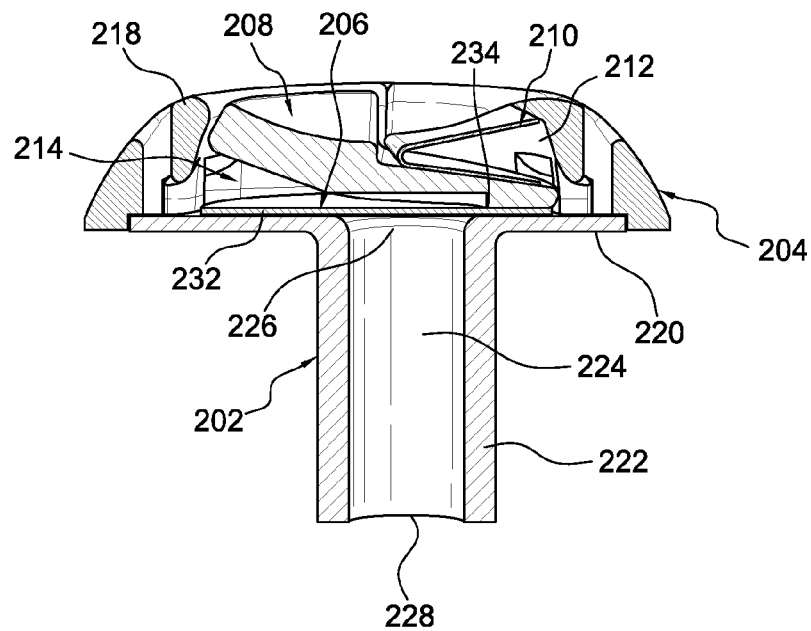
FIG. 3A is a cross-sectional view of the valve in FIG. 2 in the closed position.

In the closed position, the free part 232 and the attached part 234 of the membrane 206 are seated on the base 220 and the upper opening 226 is sealed by the membrane 206 as seen in FIG. 3A. The free part 232 can create a sealing force against the base 220 based on the material properties and/or shape of the free part 232. The attached part 234 can create a sealing force against the base 220 based on the material properties and/or shape of the attached part 234, and a biasing force exerted on the attached part 234 by the release element 208 and the resilient member 210. The membrane 206 can be configured such that a vacuum in a socket increases the sealing force of the attached part 234 and/or the free part 232 against the base 220.

The sealing area between the membrane 206 and the base 220 can be substantially greater than the area of the upper opening 226. This has the effect of improving the seal between the base 220 and the membrane 206 over the upper opening 226. The sealing area between the membrane 206 and the base 220 can be greater than about 1.1 times, about 1.2 times, about 1.5 times, about 2 times, about 3 times, about 4 times, or about 5 times. In other embodiments, the ratio between the sealing area of the membrane 206 and the area of the upper opening 226 can be larger or smaller. This advantageously allows the valve 200 to function using only one sealing part, reducing the overall profile of the valve 200.

Figure 3B:
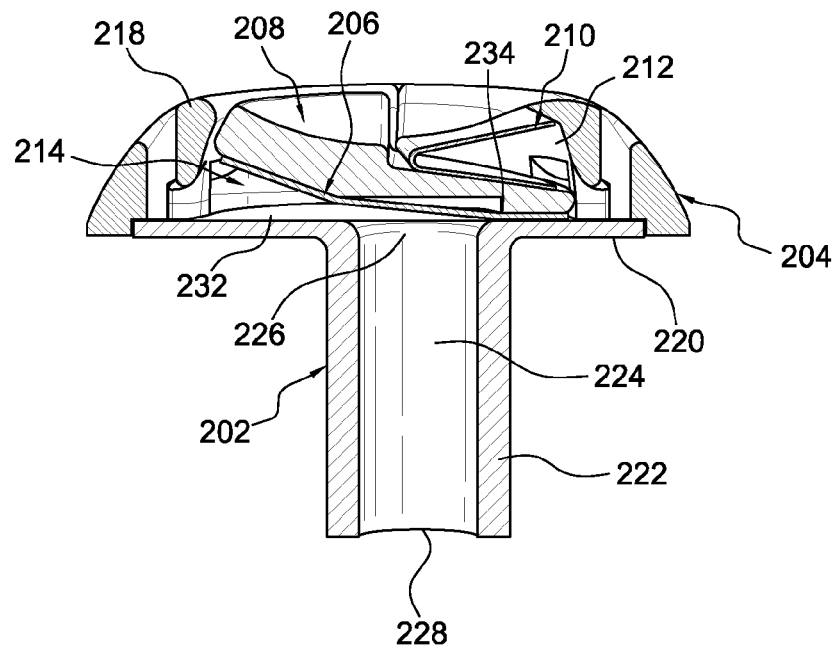
FIG. 3B is a cross-sectional view of the valve in FIG. 2 in the first open position.
Figure 3C:
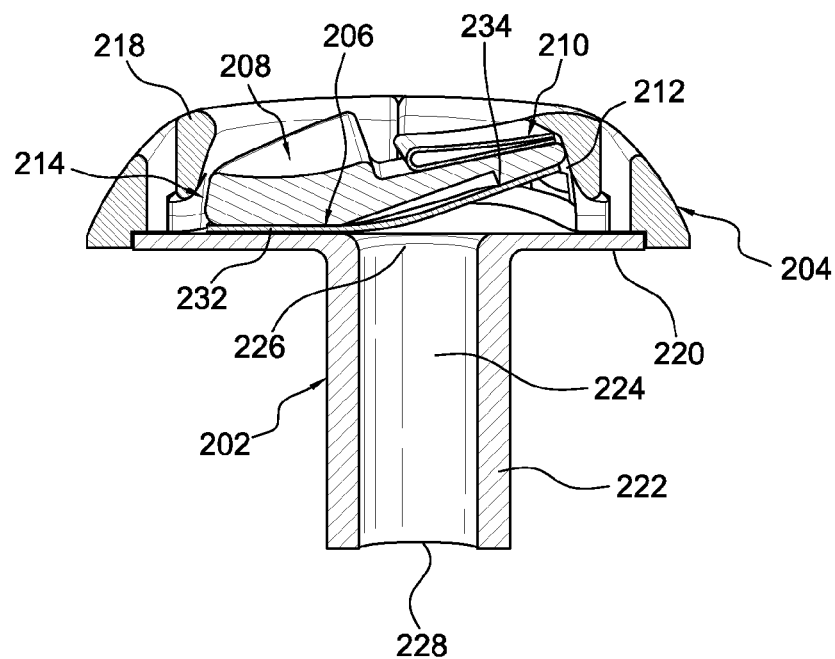
FIG. 3C is a cross-sectional view of the valve in FIG. 2 in the second open position.

In the first open position, the free part 232 lifts away from the base 220 and the upper opening 226 is unsealed as seen in FIG. 3B. In the second open position, the attached part 234 is moved away from the base 220 by the release element 208 and the opening is unsealed as seen in FIG. 3C.

The free part 232 and the attached part 234 can move the membrane 206 into the first and second open positions independently of one another and/or in response to different triggers or events. When the free part 232 of the membrane 206 lifts away from the base 220, air can exit the socket through the passageway 224. When the attached part of the membrane 206 lifts away from the base 220, air can enter or exit the socket through the passageway 224.

The free part 232 of the membrane 206 can automatically relieve a buildup of pressure inside of a socket. When the buildup of pressure inside of the socket exceeds the sealing force of the free part 232, the pressure can lift the free part 232 off of the base 220 such that the upper opening 226 is unsealed and air can flow from the socket through the passageway 224. Easy donning can be accomplished since the air is automatically and expelled as the residual limb is inserted into the socket. This is because the volume of the residual limb displaces the volume of air inside the socket, forcing the free part 232 of the membrane 206 to lift away from the base 220, and forcing the remaining air out through the passageway 224 of the valve 200.

As soon as the air is expelled from the socket, the free part 232 naturally or elastically returns to its original position on the base 220 such that any air expelled through the valve 200 cannot re-enter the socket through the passageway 224. The suspension fit of the residual limb within the socket can be preserved. The membrane 206 can be configured such that the positive pressure lifts the free part 232 away from the base 220 but not the attached part 234.

The valve 200 can permit expulsion of the air through apertures 236 (seen in FIG. 2) formed by the housing 204, with the air entering the lower opening 228 in the shaft 222, passing through the passageway 224, the upper opening 226, the interior cavity 214 of the housing 204, and exiting the apertures 236. This arrangement easily lets air expel through the valve 200. As seen in FIG. 3B, when the free part 232 of the membrane 206 is rotated away from the base 220, the shape of the bottom surface of the free part 232 above the upper opening 226 can form a flow path that redirects the air exiting the upper opening 226 toward the apertures 236. This allows the air to move more smoothly and directly out of the valve 200, reducing air resistance.

The free part 232 of the membrane 206 is arranged such that it is not under the influence of a distinct biasing force or member, as in the prior art. For instance, the pressure buildup can easily swing or lift the free part 232 away from the base 220 without having to overcome an opposing biasing member pushing the free part 232 back toward the base 220. This advantageously helps to reduce air resistance and to improve air flow through the valve 100.

The arrangement of the free part 232 can also provide partial suction created naturally during ambulation, improving suspension. For instance, air may be drawn into the interior of conventional sockets during the repeating phases of a normal gait cycle. The repetitive motions displayed between the stance and swing phases of walking generate a pumping and pistoning effect within the socket which draws in air and creates positive pressure. To combat this problem, the free part 232 can function to expel the air from the region between the socket interior and the liner-sheathed residual limb. The pressure within this space decreases as air is expelled correspondingly increasing the suction available to hold a prosthetic device to the residual limb.

The point at which the build of pressure inside of a socket triggers or lifts the free part 232 off of the base 220 can be any suitable pressure and/or can be customized based on the individual needs of the user. This pressure can be selected or set by a user, a clinician, or a medical professional.

The attached part 234 of the membrane 206 can be operated and controlled independently of the free part 232 to introduce and/or relieve pressure inside of a socket. As seen in FIG. 3C, when the release element 208 is moved to a release position, the release element 208 can lift the attached part 234 off of the base 220 such that the upper opening 226 is unsealed and air can flow from the socket through the passageway 224. When the button is released, the resilient member 210 can return the release element 208 to its normal position, which causes the attached part 234 to reseal the upper opening 226 and inhibits air flow through the passageway 224. The membrane 206 can be configured such that when the release element 208 lifts the attached part 234 away from the base 220, the free part 232 is not lifted from the base 220. The membrane 206 can be configured such that when the release element 208 lifts the attached part 234 away from the base 220, at least a portion of the free part 232 is lifted from the base 220.

Because operation of the attached part 234 is not configured to depend on the pressure inside of the socket, the attached part 234 can be actuated in negative pressure and/or positive pressure environments. If the attached part 234 is actuated when there is a pressure buildup in a socket, the air inside of the socket can escape through the valve 200. If the attached part 234 is actuated when there is a vacuum in a socket, outside air can be drawn into the socket through the valve 200. This advantageously helps break the suction between the liner-sheathed residual limb and the socket, allowing the user to quickly and easily remove the socket.

The attached part 234 of the membrane 206 is connected to the release element 208 in such a way that the attached part 234 can cover at least a portion of the opening 226 when the free part 232 moves the membrane 206 to the first open position. The free part 232 is configured such that at least a portion of the free part 232 can cover at least a portion of the upper opening 226 when the attached part 234 moves the membrane to the second open position. This advantageously allows the attached part 234 and the free part 232 to independently unseal the upper opening 226.

As best shown in FIG. 4, the release element 208 can be pivotally connected to the housing 204. The housing 204 can include a pair of pivot arm receiving recesses 238. Pivot arms 240 of the release element 208 can be positioned within the recesses 238 and pivotally connected to the housing 204. The release element 208 is rotatable about an axis extending through the pivot arms 240 between a normal position, in which a flat engagement portion 242 of the release element 208, which is connected to the attached part 234 of the membrane 206, holds attached part 234 against the base 220, and a release position, wherein the engagement portion 242 rotates away from the base 220 and lifts the attached portion 234 off of the base 220, thus manually unsealing the upper opening 226. The distance the release element 208 moves can correspond to how large of a space or flow area is formed between the attached part 234 and the upper opening 226. For instance, if a user wants to expel only a small amount of air from a socket, the user can move the release element 208 only a small distance such that a smaller flow area is formed between the attached part 234 and the upper opening 226. If a user wants to expel more air from a socket, the user can move the release element 208 a greater distance. The release element 208 can include a concave recess 246 that corresponds to the concave recess 230 of the housing 204. The release element 208 can be a release button or any other suitable type of release element.

The release element 208 can be biased toward the normal position. For instance, the resilient member 210 can be positioned between the interior surface 212 of the housing 204 and a bearing portion 244 on the upper side of the release element 208. The resilient member 210 can comprise a v-type spring including a first arm engaging the bearing portion 244 and a second arm engaging the housing 204. The resilient member 210 can be compressed between the release element 208 and the housing 204 and stored mechanical energy in the resilient member 210 can force the release element 208 toward the normal position. While a v-type spring is described, it will be appreciated that the resilient member can comprise any suitable member to bias the release element 208 toward the normal position, such as, for example a torsion spring or bar or any other suitable member.

Moving the release element 208 to the release position can let air into a socket so the socket can be doffed. The air enters the apertures 236 and channels through the fluid passageway 224 to introduce air into the socket. This advantageously helps break the suction between the liner-sheathed residual limb and the socket, allowing the user to quickly and easily remove the socket. Moving the release element 208 to the release position can also let air out of a socket so the socket can be donned. This allows a user to manually expel air from a socket so the socket can be donned.

It will be appreciated that the valve 200 is to be exemplary only, any valve is possible. While the membrane is shown comprising a disc-like member, in other embodiments, the membrane may comprise a Belleville washer, a membrane having a flexible and rigid section, a diaphragm valve, a saddle type valve, a straight through valve, a check valve, a relief valve, or any other suitable sealing element. It should be appreciated that many variations of the release element having different shapes and sizes can be used for manipulating the membrane. Although such variations may differ in form, they perform substantially similar functions. In other embodiments, the valve may include more than one passageway and over two openings. In yet other embodiments, the housing may have a cylindrical or other suitable shape.

While various aspects and embodiments have been disclosed, other aspects and embodiments are contemplated. The aspects and embodiments disclosed are for illustration and are not intended to be limiting. The words "including," "having," and variants thereof (e.g., "includes" and "has") as used, including the claims, shall be open ended and have the same meaning as the word "comprising" and variants thereof (e.g., "comprise" and "comprises").

The invention claimed is:

1. A valve for a prosthetic socket defining a socket cavity, the valve comprising:
    a body defining an upper opening, a lower opening adapted to be in fluid communication with the socket cavity, and a shaft having a passageway formed between the upper and lower openings;
    a membrane flexibly seated on the body over the upper opening and movable between a closed position, in which the upper opening is sealed by the membrane such that fluid communication between the upper opening and the lower opening is inhibited, and an open position, in which the upper opening is unsealed such that fluid can flow through the passageway, the membrane having an attached part arranged to cover a first portion of the upper opening, and a free part arranged to cover a second portion of the upper opening, the attached and free parts being defined along a length of the membrane;
    a housing secured on the body and over the membrane, and the housing defining an interior cavity;
    a release element pivotally connected to the housing and located in the interior cavity of the housing, the release element attaching to the attached part of the membrane, the release element operable within the housing to move the attached part between the open and the closed positions and the free part operable to move the membrane to the open position in response to a buildup of pressure inside the socket cavity independent of operation of the release element.

2. The valve of claim 1, wherein the release element is movable between a normal position arranged to compress the attached part against the body, and a release position arranged to lift the attached part away from the body to unseal the upper opening.

3. The valve of claim 2, further comprising a resilient member located between the housing and the release element, and the resilient member arranged to bias the release element.

4. The valve of claim 3, wherein the resilient member is arranged to bias the release member relative to the normal position such that a flat engagement portion of the release element connecting to the attached part holds the attached part against the base.

5. The valve of claim 1, wherein at least a portion of the attached part covers the first portion of the upper opening when the free part moves the membrane to the open position.

6. The valve of claim 1, wherein at least a portion of the free part covers the upper opening when the attached part moves the membrane to the open position.

7. The valve of claim 1, wherein the membrane comprises an elastomeric disc.

8. The valve of claim 1, wherein the free part is arranged so a pressure build up in the socket cavity lifts the free part without unsealing the attached part of the membrane away from the upper opening.

9. The valve of claim 1, wherein an exterior surface of the housing defines a first concave recess thereon.

10. The valve of claim 9, wherein the release element defines a second concave recess substantially corresponding to the concave recess of the housing.

11. The valve of claim 1, wherein the release element defines at least one pivot arm received by and pivotally connected to the housing.

12. The valve of claim 1, wherein the housing defines a plurality of through apertures in fluid communication with the interior cavity.

13. The valve of claim 12, wherein a bottom surface of the release element directs fluid flow through at least one of the through apertures when the release element is in a release position which is arranged to lift the attached part away from the body to unseal the first opening.

14. The valve of claim 1, wherein an end portion of the release element only attaches to the attached part of the membrane.

15. The valve of claim 14, wherein the attached part of the membrane is located at an end portion of the membrane at a side opposite the free part of the membrane.

16. The valve of claim 1, wherein the release element has first and second end portions, the first end portion extending over the free part of membrane, and the second end portion attaching to the attached part of the membrane.

17. The valve of claim 16, wherein the release element pivots generally at a location between the first and second end portions.

18. A valve for a prosthetic socket defining a socket cavity, the valve comprising:
- a body defining an upper opening, a lower opening adapted to be in fluid communication with the socket cavity, and a shaft having a passageway formed between the upper and lower openings;
- a membrane flexibly seated on the body over the upper opening and movable between a closed position, in which the upper opening is sealed by the membrane such that fluid communication between the upper opening and the lower opening is inhibited, and an open position, in which the upper opening is unsealed such that fluid can flow through the passageway, the membrane having an attached part arranged to cover a first portion of the upper opening, and a free part arranged to cover a second portion of the upper opening, the attached and free parts being defined along a length of the membrane;
- a housing secured on the body and over the membrane, and the housing defining an interior cavity and a plurality of through apertures in fluid communication with the interior cavity;
- a release element pivotally connected to the housing and located in the interior cavity of the housing, the release element attaching to the attached part of the membrane, the release element operable within the housing to move the attached part between the open and the closed positions independent of the free part.

19. A valve for a prosthetic socket defining a socket cavity, the valve comprising:
- a body defining an upper opening, a lower opening adapted to be in fluid communication with the socket cavity, and a shaft having a passageway formed between the upper and lower openings;
- a membrane flexibly seated on the body over the upper opening and movable between a closed position, in which the upper opening is sealed by the membrane such that fluid communication between the upper opening and the lower opening is inhibited, and an open position, in which the upper opening is unsealed such that fluid can flow through the passageway, the membrane having an attached part arranged to cover a first portion of the upper opening, and a free part arranged to cover a second portion of the upper opening, the attached and free parts being defined along a length of the membrane;
- a housing secured on the body and over the membrane, and the housing defining an interior cavity and a plurality of through apertures in fluid communication with the interior cavity;
- a release element pivotally connected to the housing and located in an interior cavity of the housing, the release element having a first end attaching to the attached part of the membrane located at an end portion thereof on an opposite side of the free part, and a second end extending over the free part, the release element pivotable within the housing to move the attached part between the open and the closed positions, and the free part operable between the open and closed positions independent of the attached part.

* * * * *